US011120913B2

(12) United States Patent
Dey et al.

(10) Patent No.: US 11,120,913 B2
(45) Date of Patent: Sep. 14, 2021

(54) EVALUATING DRUG-ADVERSE EVENT CAUSALITY BASED ON AN INTEGRATION OF HETEROGENEOUS DRUG SAFETY CAUSALITY MODELS

(71) Applicant: International Business Machines Corporation, Armonk, NY (US)

(72) Inventors: Sanjoy Dey, White Plains, NY (US); Achille B. Fokoue-Nkoutche, White Plains, NY (US); Katherine Shen, New York, NY (US); Ping Zhang, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 405 days.

(21) Appl. No.: 15/878,523

(22) Filed: Jan. 24, 2018

(65) Prior Publication Data

US 2019/0228864 A1    Jul. 25, 2019

(51) Int. Cl.
*G16H 50/30* (2018.01)
*G16H 50/50* (2018.01)
(Continued)

(52) U.S. Cl.
CPC ............. *G16H 50/30* (2018.01); *G16H 10/60* (2018.01); *G16H 20/10* (2018.01); *G16H 50/50* (2018.01); *G16H 70/40* (2018.01)

(58) Field of Classification Search
CPC ........ G16H 20/10; G16H 50/20; G16H 50/30; G16H 50/50; G16H 10/60
See application file for complete search history.

(56) References Cited

U.S. PATENT DOCUMENTS

| 9,305,267 B2 * | 4/2016 | Tatonetti | G16H 50/50 |
| 2006/0111847 A1 * | 5/2006 | Pearson | G16H 10/20 |
| | | | 702/19 |

(Continued)

FOREIGN PATENT DOCUMENTS

| AU | 2015213399 A1 * | 3/2016 | G16H 10/60 |

OTHER PUBLICATIONS

Ji et al., A Fuzzy Recognition-Primed Decision Model-Based Causal Association Mining Algorithm for Detecting Adverse Drug Reactions in Postmarketing Surveillance, 2010, IEEE, 978-1-4244-8126-2/10 (Year: 2010).*

(Continued)

*Primary Examiner* — Elaine Gort
*Assistant Examiner* — Constantine B Siozopoulos
(74) *Attorney, Agent, or Firm* — Stephen J. Walder, Jr.; William J. Stock

(57) ABSTRACT

Mechanisms are provided that implement a plurality of heterogeneous causality models and a metaclassifier for predicting a likelihood of causality between a drug and an adverse event (AE). The plurality of heterogenous causality models process drug information to generate a plurality of risk predictions for a drug and AE pair. The risk predictions include a risk score or a risk label indicating a probability of the AE occurring with use of the drug. The plurality of heterogenous causality models provide risk predictions, associated with the drug and AE pair, to a metaclassifier which generates a single causality score value indicative of a probability of causality between the drug and the AE, of the drug and AE pair, based on an aggregation of the risk predictions from the plurality of heterogenous causality models. The metaclassifier outputs the single causality score value in association with information identifying the drug and AE pair.

20 Claims, 4 Drawing Sheets

(51) Int. Cl.
    *G16H 20/10*     (2018.01)
    *G16H 10/60*     (2018.01)
    *G16H 70/40*     (2018.01)

(56) References Cited

U.S. PATENT DOCUMENTS

| | | | |
|---|---|---|---|
| 2011/0125734 A1 | 5/2011 | Duboue et al. | |
| 2013/0179375 A1* | 7/2013 | Tatonetti | G06N 20/00 706/12 |
| 2014/0074509 A1* | 3/2014 | Amarasingham | G16H 50/30 705/3 |
| 2017/0116376 A1 | 4/2017 | Fokoue-Nkoutche et al. | |
| 2017/0316175 A1* | 11/2017 | Hu | G06N 5/022 |
| 2018/0004902 A1* | 1/2018 | Aronow | G16H 70/40 |

OTHER PUBLICATIONS

Ji et al., A Fuzzy Recognition-Primed Decision Model-Based Causal Association Mining Algorithm for Detecting Adverse Drug Reactions in Postmarketing Surveillance, 2010, IEEE, 978-1-4244-8126-2/10 (Year: 2010) (Year: 2010).*

Liu et al., Large-scale prediction of adverse drug reactions using chemical, biological, and phenotypic properties of drugs, Journal of the American Medical Informatics Association, vol. 19, Issue e1, Jun. 2012, pp. e28-e35 (Year: 2012).*

Ji et al., A Fuzzy Recognition-Primed Decision Model-Based Causal Association Mining Algorithm for Detecting Adverse Drug Reactions in Postmarketing Surveillance, 2010, IEEE, 978-1-4244-8126-2/10 (Year: 2010) (Year: 2010) (Year: 2010).*

Liu et al., Large-scale prediction of adverse drug reactions using chemical, biological, and phenotypic properties of drugs, Journal of the American Medical Informatics Association, vol. 19, Issue e1, Jun. 2012, pp. e28-e35 (Year: 2012) (Year: 2012).*

Agbabiaka, Taofikat B., Jelena Savović, and Edzard Ernst. "Methods for causality assessment of adverse drug reactions." Drug safety 31.1 (2008): 21-37. (Year: 2008).*

Agbabiaka, Taofikat B. et al., "Methods for Causality Assessment of Adverse Drug Reactions: A Systematic Review", Drug Safety 2008, 31 (1): Jan. 2008, pp. 21-37.

Arimone, Yannick et al., "Inter-expert agreement of seven criteria in causality assessment of adverse drug reactions", British Journal of Clinical Pharmacology, Oct. 2007, 64:4, pp. 482-488.

Danan, Gaby et al., "Causality assessment of adverse reactions to drugs—I. A novel method based on the conclusions of international consensus meetings: Application to drug-induced liver injuries", Journal of Clinical Epidemiology 1993, vol. 46 No. (11):1, Nov. 1993, pp. 1323-1330.

Dey, Sanjoy et al., "Identifying Chemical Substructures Associated with Adverse Drug Reactions", filed Apr. 21, 2017, U.S. Appl. No. 15/494,027.

High, Rob, "The Era of Cognitive Systems: An Inside Look at IBM Watson and How it Works", IBM Corporation, Redbooks, Dec. 12, 2012, 16 pages.

Liu, Mei et al., "Large-scale prediction of adverse drug reactions using chemical, biological, and phenotypic properties of drugs", Journal of the American Medical Informatics Association, 19(e1), Jun. 2012, pp. e28-e35.

Luo, Heng et al., "Prediction and Generation of Hypotheses on Relevant Drug Targets and Mechanisms for Adverse Drug Reactions", filed Aug. 8, 2017, U.S. Appl. No. 15/671,898.

Macedo, A.F. et al., "Causality assessment of adverse drug reactions: comparison of the results obtained from published decisional algorithms and from the evaluations of an expert panel, according to different levels of imputability", Journal of Clinical Pharmacy and Therapeutics, Apr. 2003, 28(2): pp. 137-143.

Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

List of IBM Patents or Patent Applications Treated as Related, Oct. 29, 2018, 2 pages.

\* cited by examiner

EVALUATING DRUG-ADVERSE EVENT CAUSALITY BASED ON AN INTEGRATION OF HETEROGENEOUS DRUG SAFETY CAUSALITY MODELS

BACKGROUND

The present application relates generally to an improved data processing apparatus and method and more specifically to mechanisms for evaluating drug-adverse event causality based on an integration of heterogenous drug safety causality models.

Adverse drug reactions, or ADRs, are injuries caused to a patient because of the patient taking a medication. An adverse event (AE), or adverse drug event (ADE), refers to any injury occurring at the time the patient is taking a drug, whether or not the drug itself is identified as the cause of the injury. Thus, an ADR is a special type of AE in which a causative relationship can be shown between the drug and the adverse reaction.

ADRs may occur following a single dose of the medication (drug) or due to a prolonged administration of a drug, and may even be caused by the interaction of a combination of two or more drugs that the patient may be taking. This is different from a "side effect" in that a "side effect" may comprise beneficial effects whereas ADRs are universally negative. The study of ADRs is the concern of the field known as pharmacovigilance.

Currently, the evaluation of a case, i.e. a combination of a patient's electronic medical records from one or more electronic medical record source computing systems, for identifying adverse drug reactions, i.e. the causality of an adverse reaction with a particular drug being taken, is a highly manual process in which a human subject matter expert (SME) reviews the case and comes to a decision as to whether there is a causal relationship between a drug and an adverse reaction. However, this decision requires an evaluation of a large number of criteria and, being a manual process, is both time consuming and error prone.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions that are executed by the at least one processor to cause the at least one processor to be configured to implement a plurality of heterogeneous causality models and a metaclassifier for predicting a likelihood of causality between a drug and an adverse event (AE). The method comprises processing, by the plurality of heterogenous causality models, drug information for the drug to generate a plurality of risk predictions for a drug and AE pair. The risk predictions include at least one of a risk score or a risk label indicating a probability of the AE occurring with use of the drug. The method further comprises providing, by the plurality of heterogenous causality models, the risk predictions, associated with the drug and AE pair, to a metaclassifier and generating, by the metaclassifier, a single causality score value indicative of a probability of causality between the drug and the AE, of the drug and AE pair, based on an aggregation of the risk predictions from the plurality of heterogenous causality models. In addition, the method comprises outputting, by the metaclassifier, the single causality score value in association with information identifying the drug and AE pair.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
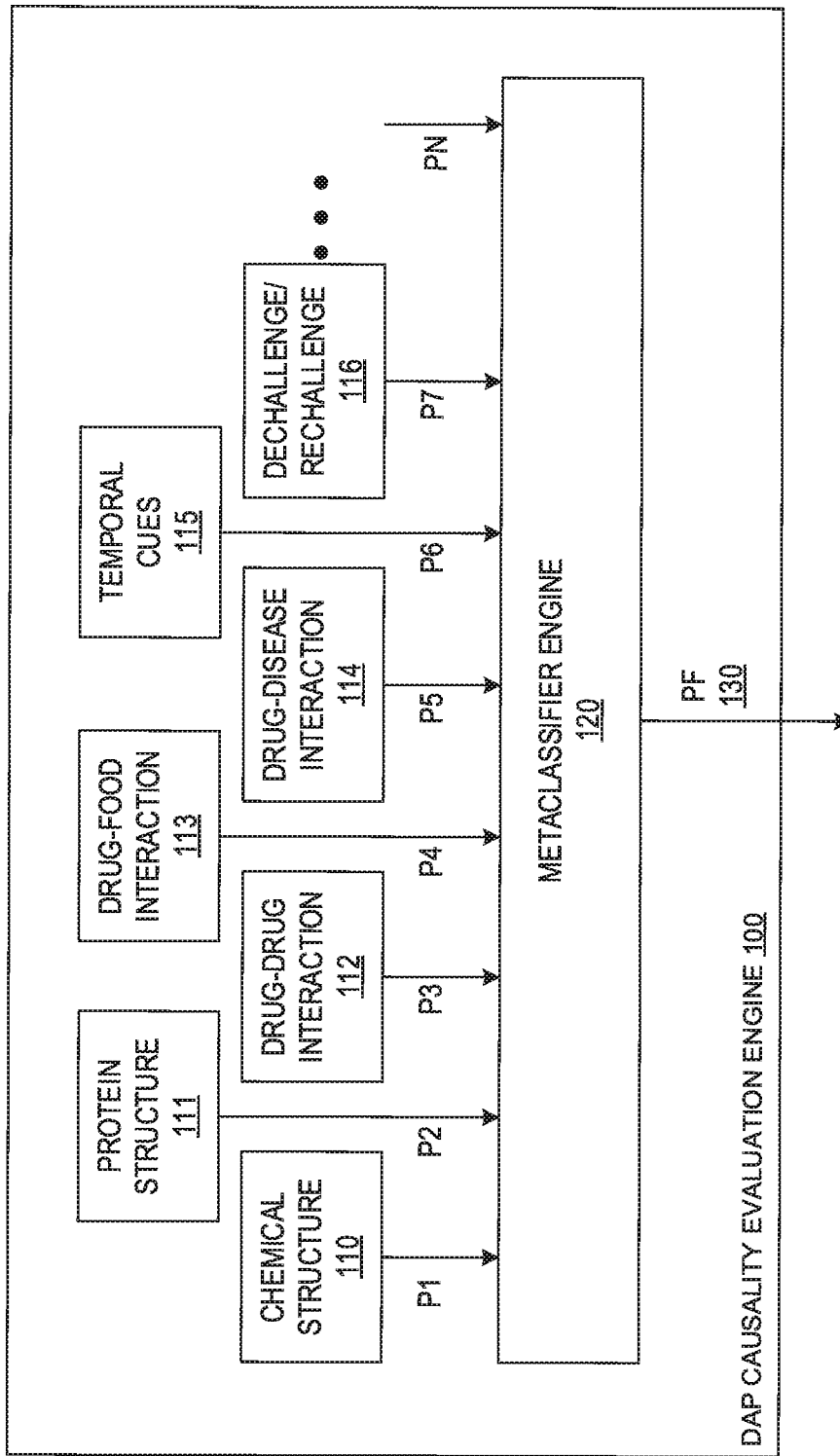
FIG. 1 is an example block diagram illustrating components of a drug-adverse event (AE) pair causality evaluation engine in accordance with one illustrative embodiment.

Causality assessment is vital to pharmacovigilance processes in the pharmaceutical industry and plays a role in important decisions, such as whether to make a change in a drug label. Moreover, causality assessment is important in other aspects of the practice of medicine, such as making decisions as to a patient's treatment, diagnosing the cause of adverse events (AE) with regard to drugs that are taken, and the like. Causality is assessed qualitatively by individual subject matter expert (SME) contributors based on their own individual expertise, with little or no interaction of the contributors with one another. As a result, there is low inter-contributor agreement, i.e. two different subject matter experts may disagree as to the qualitative assessment of causality between a drug and an adverse event (AE) (or adverse drug reaction (ADR)).

Moreover, because of the manual qualitative evaluation based on individual human SME experience and expertise, there is a large variation in the evaluations, some of which may be erroneous due to human error or a lack of consideration of all possible factors since causality is a very complex evaluation which may require evaluation of a large number of different factors. For example, the Council for International Organizations of Medical Sciences (CIOMS) has specified the following criteria for evaluating drug safety:

1. Criteria to consider when reviewing a signal, i.e. an indicator of an adverse drug reaction (ADR) from a case series (e.g., a set of patient electronic medical record (EMR) data for a patient) or other sources:
   Rechallenge/Dechallenge (a medical testing protocol in which a medicine or drug is administered, withdrawn, then re-administered, while being monitored for adverse effects at each stage); known mechanism, e.g., class effect (a drug effect produced by all members of a chemically related group of medications and not only by a single drug from that class); biological plausibility (i.e. the proposal of a causal relationship); consistent time-to-onset (temporality); observed in drug-drug, drug-disease, drug-food interaction, etc.
2. Clinical data:
   Pharmacodynamic, pharmacokinetic, and/or interaction studies; consistent outcome in study investigating drug-AE association; etc.
3. Preclinical data in well-designed studies:
   Similar findings in animals; positive in vitro or ex vivo tests.
4. Product quality data.

Each of these categories of criteria may comprise a large number of individual parameters and characteristics, and combinations of parameters and characteristics, that may influence the evaluation of the criteria.

The illustrative embodiment provides a drug-adverse event causality evaluation engine which leverages the computing power of specifically configured computing systems as well as cognitive logic that emulates the thinking processes of human beings, to specifically identify causal relationships between drugs and adverse events, or adverse drug reactions (ADRs), taking into account the large number of criteria and complex relationships between various properties of the drugs and adverse reactions, so as to automatically identify adverse drug reactions (ADRs) that have a causal link to the taking of the drug by patients. The ADRs may then be used to inform pharmaceutical providers that may provide the drug, so that they may make modifications to guides, drug labels, or other documentation associated with the drug based on the identified causal links between the drug and ADRs, or even make modifications to the drug itself. In some illustrative embodiments, the output of the causal relationships may be used to inform medical personnel of the ADRs so that appropriate treatment of the patient may be performed. Moreover, in some illustrative embodiments, the identified ADRs may be input to other cognitive logic for performance of cognitive operations to support decision making, such as in a decision support system.

In one illustrative embodiment, mechanisms are provided for automatically assessing a drug and an adverse event (AE) pair causality using chemical structure properties, drug-drug interaction properties, and protein structure properties, as well as several patient and disease characteristics, e.g., drug-food interaction, drug-disease interaction, temporal cues, dechallenge/rechallenge characteristics, etc., which may be provided in the patient's electronic medical records (EMRs). These are collectively referred to as "causality factors" herein. Causality prediction scores are calculated with regard to these various causality factors based on a plurality of causality models, each causality model being specifically configured and trained to evaluate specific ones of the causality factors and generate a corresponding causality prediction score for that causality factor.

The causality prediction scores are integrated by meta-classifier logic that is configured and trained to combine the causality prediction scores by applying learned weightings to the various causality prediction scores and other manipulations, so as to generate a single final causality score for the drug and AE pairing that identifies a single coherent assessment of causality of the drug-AE pair. Thus, the illustrative embodiment provides a metaclassifier mechanism that integrates multiple ADR causality prediction scores from a plurality of heterogeneous causality models that evaluate the drug safety with regard to particular causality factors, and generates a single coherent assessment of causality for the drug-AE pair. It should be appreciated that the AE in the drug-AE pairing may comprise an adverse drug reaction (ADR) and thus, the drug-AE pairing and corresponding causality prediction may in fact be a prediction of the drug-ADR pairing, i.e. given this drug and the patient's causality factors, the prediction indicates a likelihood that the ADR is caused by the drug or that the ADR will be caused by the taking of the drug by the particular patient.

The causality prediction provides a score that is indicative of the likelihood that the AE is caused by the taking of the drug in the drug-AE pairing. The single integrated causality prediction score may be evaluated against one or more threshold values indicating a minimum causality prediction score required to identify a valid causality link between a drug and AE in the drug-AE pair. If the integrated causality prediction score meets or exceeds the threshold value, then it may be regarded as an actual valid causality link indicating that the drug is a cause of the AE (or ADR) for this patient. If the integrated causality prediction score does not meet the threshold value, then the drug-AE pair does not represent a valid causality link of the drug with the AE for this patient. A corresponding notification or output of the results of such a comparison may be generated indicating whether or not a valid causality link exists between the drug and the AE (or ADR).

This evaluation of drug-AE pairs may be done for each possible drug-AE pair being considered, e.g., a listing of drugs to be considered and a particular AE, or a particular drug to be considered and a listing of particular AEs to be considered. Thus, in one sense, a user may wish to know all the possible AEs (or ADRs) that have a relatively high likelihood of being caused by the taking of a particular drug with patients of various characteristics, or with regard to a particular patient, i.e. a particular set of patient characteristics. In another sense, a user may wish to know, for a given AE, what drugs the patient is taking that may have caused the AE. In some cases, the drug-AE pairings may be evaluated with regard to multiple drugs and multiple AEs so as to determine particular combinations of drugs that the patient may be taking that each may be contributing to particular AEs (or ADRs) the patient is experiencing or is likely to experience.

Because the mechanisms of the illustrative embodiments provide automated specialized computing systems for performing drug-AE (or ADR) pair evaluations, the mechanisms of the illustrative embodiments may evaluate a relatively large and complex set of causality factors that is not feasible for the previous manual evaluations. Moreover, the automated specialized computing systems further allow for such evaluations that do not suffer from the drawbacks of human error, which is likely in the previous manual evaluations. Furthermore, such evaluations may be performed much more quickly and with regard to a relatively larger number of possible drug-AE pairs. All of these improvements serve to improve the decision making of medical personnel by providing decision support services that provide additional information upon which the medical personnel may base their treatment decisions for a particular patient. Moreover, in some illustrative embodiments, the improvements improve the operation of a cognitive system when performing decision support services such as diagnostic services, treatment recommendation services, or the like.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general-purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine-readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for evaluating drug-adverse event causality based on an integration of heterogenous drug safety causality models. FIG. 1 is an example block diagram illustrating components of a drug-adverse event (AE) pair causality evaluation engine in accordance with one illustrative embodiment. As shown in FIG. 1, the drug-AE pair (DAP) causality evaluation engine 100 comprises a plurality of individual heterogeneous causality models 110-116 which each provide specially configured logic for evaluating a specific set of one or more causality factors with regard to DAP causality. Each of the causality models 110-116 generates an output of a detailed interpretation of the causal factors, or features, e.g., specific substructures of the drug, specific proteins which bind the drug, etc., via feature selection technology and statistical tests. Moreover, the output of each of the causality models 110-116 comprises a component causality score and corresponding risk label that represents the predicted probability of the drug causing the corresponding adverse event from the perspective the causal factors or features evaluated by the particular causality model 110-116.

In general, the causality models 110-116 may each be constructed, for example, as logistic regression models that evaluate various features specific to those causality models. The logistic regression models may operate based on training repositories comprising information obtained from structured data sources (e.g., drugs.com website) and/or unstructured data sources (e.g., literature, Wikipedia™, other natural language content sources, etc.). Multi-dimensional drug profiles may be generated from multiple structured and/or unstructured data sources to perform the various comparisons performed by the causality models 110-116. A logistic regression model for the particular causality model 110-116 may be built using features from these drug profiles, and profiles of other structures (e.g., other drug profiles, protein structure profiles, food nutrient profiles, disease feature profiles, etc.), and known interactions, which are used to train the logistic regression models to predict interactions and associated risk scores for corresponding adverse events or adverse drug reactions.

For example, the causality models 110-116 may comprise a chemical structure causality model 110 that operates to evaluate the chemical structure of the drug using medical knowledge of chemical structures and the way in which they affect patients, to generate a prediction as to whether a particular chemical structure is likely to cause an adverse drug reaction in a particular patient. The chemical structure causality model 110 may receive as input a two dimensional or three-dimensional chemical structure of the drug and output, for each drug-adverse drug reaction (ADR) pairing, a prediction score which indicates the probability that the drug may cause the ADR from the viewpoint of the chemical structure of the drug itself. An example of a chemical structure causality model which may be used as causality model 110 in some illustrative embodiments is described in commonly assigned and co-pending U.S. patent application Ser. No. 15/494,027, which is hereby incorporated herein by reference.

The causality models 110-116 may further comprise a protein structure causality model 111 that operates to evaluate the chemical-protein binding for a predetermined set of proteins. For example, the protein structure causality model 111 may receive as input the two-dimensional or three-dimensional chemical structure of the drug and a predetermined collection of human protein structures (also two or three dimensional), e.g., a set of approximately 600 human protein structures, although any number of protein structures may be utilized. For each drug-ADR pairing, the protein structure causality model 111 may generate a prediction score which indicates the probability that the drug causes the ADR from the viewpoint of the chemical-protein bindings. An example of a protein structure causality model which may be utilized as causality model 111 in one illustrative embodiment is described in commonly assigned and co-pending U.S. patent application Ser. No. 15/671,898, which is hereby incorporated herein by reference.

The causality models 110-116 may also comprise a drug-drug interaction causality model 112. The drug-drug interaction causality model 112 may utilize drug interaction information which may be found in natural language documentation such as clinical statements, guidelines, and in some patient statements, with this information being extracted from such sources using natural language processing mechanisms. Drug-to-drug interaction information may also be provided by drug manufacturers, health organizations, governmental organizations, and other sources in various forms. One example of a source of drug information that includes drug-to-drug interaction information, is the Gold Standard Drug Database, available from Elsevier. One example embodiment for implementing a drug-drug interaction causality model 112 is described in co-pending and commonly assigned U.S. Patent Publication No. 2017/0116376, entitled "Prediction of Adverse Drug Events," published on Apr. 27, 2017.

The causality models 110-116 may comprise a drug-food interaction causality model 113 that operates to predict drug-food interactions through large-scale similarity-based link prediction. The drug-food interaction causality model 113 may construct multiple drug-drug similarities, and multiple food-food similarities from heterogeneous data, calculate drug-food feature vectors based on heterogeneous drug-drug/food-food similarities, build machine learning models based on drug-food feature vectors, and output prediction scores for new drug-food pairs. These similarities may be based on the drugs' chemical similarities and the foods' nutrient similarities.

The other causality models 110-116 may similarly provide logic for evaluating the causality between various interactions and evaluation factors, such as drug-disease interactions 114, temporal cues 115, and dechallenge/rechallenge 116. For example, the causality model 110-116 may be built by constructing a drug-food interaction training repository from multiple structured (e.g., drugs.com) and unstructured (e.g., literature, Wikipedia™) data sources, and constructing multi-dimensional drug profiles and multiple drug similarity measures from multiple structured and unstructured data sources to compare drugs. These similarity measures may comprise, for example, chemical structure similarity, drug target based similarities, chemical—protein interactome (CPI) profiles based similarity, drug mechanism of action based similarity, and the like. The building of the drug-food causality model 113 may further involve constructing multi-dimensional food profiles and multiple food similarity measures from multiple structured and unstructured data sources to compare foods. These similarity measures may include, for example, composition similarity, nutrients similarity, taxonomy similarity, and the like. The building of the drug-food causality model 113 may also further involve constructing multi-dimensional drug-food profiles and pair-similarity measures to compare drug-food pairs by combining drug similarity measures and food similarity measures generated as discussed above. The causality model 113 may be built by building an adjusted logistic regression model by using features from the multi-dimensional drug-food profiles and pair-similarity measures as features, and known drug-food interactions from the drug-food interaction training repository as training labels. The drug-food causality model predicts whether a drug and food interact or not, and provides an output risk score indicating a probability of an adverse drug reaction or adverse event.

Similar causality models for drug-disease interactions, temporal cues, and dechallenge/rechallenge may be generated using logistic regression models to provide the plurality of causality models 110-116 which operate to evaluate various types of characteristics of the drug and generate predictions as to the drug causing an adverse event or adverse drug reaction from the viewpoint of those particular characteristics.

Predictions for a given drug-AE pair (DAP) comprise a causality score, e.g., a likelihood of the prediction from each data source, and a risk label, e.g., a binary indicator of whether the adverse event happens or not, with these predictions being references herein as P1, P2, . . . , Pn. The predictions are obtained from the plurality of causality models 110-116 and are provided as input to a metaclassifier engine 120 which uses a logistic regression as base-classifier with P1, P2, . . . Pn as inputs and known drug-AE pairs from a ground truth or trusted source, e.g., Federal Food and Drug Administration (FDA) drug labels (e.g., SIDER or DailyMed) as training labels to train the metaclassifier engine 120. The metaclassifier engine 120 leverages coefficients as weights of the multiple predictions from the various causality models 110-116. The metaclassifier engine 120 outputs a prediction score Pf 130 as a single coherent assessment of causality for the drug-AE pair.

For example, in one illustrative embodiment, assume that there are m drugs, n AEs (or ADRs), and k different causality models to assess the likelihood of drug-AE (or ADR) associations. For each AE, a logistic regression model may be built, $Y=f(X)$, where X is a m-by-k matrix with each row being a particular drug in the m drugs, and each column is a causality model such that each cell in the matrix $X(i,j)$ represents the risk prediction score of drug i generated by the causality model j. Here, Y is a m-by-1 vector, with all contents of the vector being binary, e.g., 1 meaning that the drug is known to cause the AE, and 0 means that the drug is unknown to cause the AE (such information may be obtained from drug label information available from various data sources, such as DailyMed, SIDER, the FDA, etc.

Since both X and Y are known, a logistic regression model may be used to learn the function f for each AE (or ADR). The coefficients of the logistic regression model serve as weights of different causality models. Since there are n AEs (or ADRs) in total, and a causality model is built for each AE (or ADR), there are n functions which serve as input to the metaclassifier which integrates or aggregates the individual causality model outputs to generate the prediction score Pf 130 as a single coherent assessment of causality for the drug-AE pair.

The output Pf 130 may be provided to a user in an output notification to indicate the predicted probability that the drug will cause the adverse event, or adverse drug reaction. Moreover, the supporting evidence for this determination, comprising the features extracted, and output along with the component causality scores and risk labels, by each of the causality models 110-116. This information may be output such that the user may drill down into the components driving the Pf 130 output to identify the individual component causality scores and risk labels and their corresponding extracted features so that the user can determine the basis for the prediction.

In one illustrative embodiment, the output Pf 130 may be provided to a user that reviews the output Pf 130, and may drill down into the output, to make determinations as to whether, and how, to modify documentation accompanying the particular drug of the drug-AE pair. For example, the user may review the output notification containing the output Pf 130 and the corresponding supporting evidence and determine a modification to the drug label to be used with the dispensing of the drug, inserted drug information in the packaging of the drug, guideline document modifications for dissemination to medical guideline providers, and the like. As an example, if it is determined that the drug has a high likelihood of causing a particular adverse drug reaction when the patient has certain characteristics, then a corresponding warning of this potential adverse drug reaction may be added to the drug label, included in the drug information insert of the packaging, and/or added to guidelines for administering the drug which may be disseminated to medical personnel via a guideline document provider, whether electronic or in printed form.

In one illustrative embodiment, the DAP causality evaluation engine 100 may operate in conjunction with a cognitive system, such as a decision support system, to provide additional decision support services for assisting medical personnel when evaluating and treating patients. For example, in one illustrative embodiment, the DAP causality evaluation engine 100 may receive, from a cognitive healthcare system, a listing of drugs that are currently being taken by a particular patient, an indication of an adverse event that is to be evaluate, and/or specific patient characteristics that may be represented as data structures in patient electronic medical records (EMRs). It should be appreciated that the cognitive healthcare system need not provide both the listing of drugs and adverse event and may in fact only provide one of these, e.g., just the adverse event or just the listing of drugs that the patient is currently taking. Alternatively, the cognitive healthcare system may provide an indication of a particular drug being considered for administration to the patient, which is to be evaluated by the DAP causality evaluation engine 100.

The listing of drugs, the individual drug of interest, and/or the adverse event may be evaluated via the DAP causality evaluation engine 100, potentially with characteristics of the patient for which the evaluation is being performed, so as to determine a probability that the drug will cause a corresponding adverse event (e.g., adverse drug reaction) for this particular patient, or will cause the specified adverse event. For example, assume that a patient comes into a physician's office complaining of a particular adverse event, e.g., a particular adverse drug reaction such as a rash, increased heart rate, etc. The drugs that the patient is currently taking may be included in the patient's EMRs and/or may be obtained from a questionnaire or interaction between the physician and the patient. The combination of the listing of drugs being taken by the patient and the adverse event identification may be provided as input to the DAP causality evaluation engine 100 which may process the drug-AE pairings generated from the listing of drugs and the specified AE to determine a prediction as to whether the particular drug is a causal factor for causing the specified AE, and provide the evidence supporting the prediction.

As another example, assume that the listing of drugs being taken by the patient are obtained from the patient EMR, and that the user wishes to obtain a listing of potential AEs that are likely to be encountered by the particular patient. The DAP causality evaluation engine 100 may generate drug-AE pairings for each drug and each potential AE which may then be evaluated automatically by the DAP causality evaluation engine 100 to generate predictions for each of the drug-AE pairings for this particular patient. As mentioned above, thresholds may be employed for filtering the drug-AE pairings to only those that have predictions with the integrated causality scores that meet or exceed the thresholds. Those remaining may be ranked relative to one another to represent to the user the most likely AEs associated with the taking of the particular drug by this patient.

In still another example, a listing of AEs associated with the patient may be obtained from the patient, the patient's EMR, or any other suitable source. The AEs and characteristics of the patient may be input to the DAP causality evaluation engine 100 which may then identify the most likely drugs that may be causing the AEs. Such a situation may be beneficial in cases where it may not be known what drugs the patient may have taken, such as in situations where the patient may be unconscious or have a mental deficiency or memory issue that may cause it to be difficult to get an accurate identification of drugs taken by the patient.

Thus, the output Pf 130 may be input to a cognitive system which operates on the output Pf 130 as an input factor indicative of a probability prediction of a causal relationship between the drug and the adverse event. A plurality of outputs Pf 130 of this nature may be obtained from the DAP causality evaluation engine 100 for a variety of different drug-AE pairings and each of them may be evaluated individual and/or together by the cognitive system to perform a cognitive operation. The cognitive operation may comprise any decision support operation that assists medical personnel in treating a patient. For example, the decision support operation may comprise a diagnosis of the patient's medical condition, e.g., a medical condition that may be at least partially caused by an adverse drug reaction to a drug being taken by the patient, a treatment recommendation where the treatment may comprise drug components that may be evaluated with regard to the various predictions for the drug-AE pairings, or the like. The predictions generated by the DAP causality evaluation engine 100 for each of the considered drug-AE pairings may be used as a further basis for evaluating diagnoses, treatments, and the like.

It should be appreciated that the DAP causality evaluation engine 100 may integrate any number of causality models 110-116 and may customize its operation with regard to a particular stage of causality assessment, which may be specified as an input parameter to the DAP causality evaluation engine 100. For example, during early drug development stage, relatively less numbers of causality factors may be evaluated, e.g., only the chemical structure information available may be evaluated by the DAP causality evaluation engine 100. For later drug development stages, more causality factors may be employed, e.g., animal models, clinical data, and the like. In embodiments where the DAP causality evaluation engine 100 is used to provide decision support services for cognitive systems when diagnosing or treating patients, the majority or even all of the causality models 110-116 may be enabled and utilized. Thus, various ones of the causality models 110-116 may be enabled for different stages of development of drugs.

Thus, the illustrative embodiments provide automated specialized computing systems for performing drug-AE (or ADR) pair evaluations which may be used to automatically evaluate a relatively large and complex set of causality factors. The automated specialized computing systems allow for such evaluations that do not suffer from the drawbacks of human error and allows such evaluations to be made quickly. The causality factors considered may be tailored to the particular stage of drug development and/or whether or not the illustrative embodiment is utilized with a cognitive system to assist in decision making support operations for assisting with the diagnosis or treatment of a particular patient.

Figure 2:
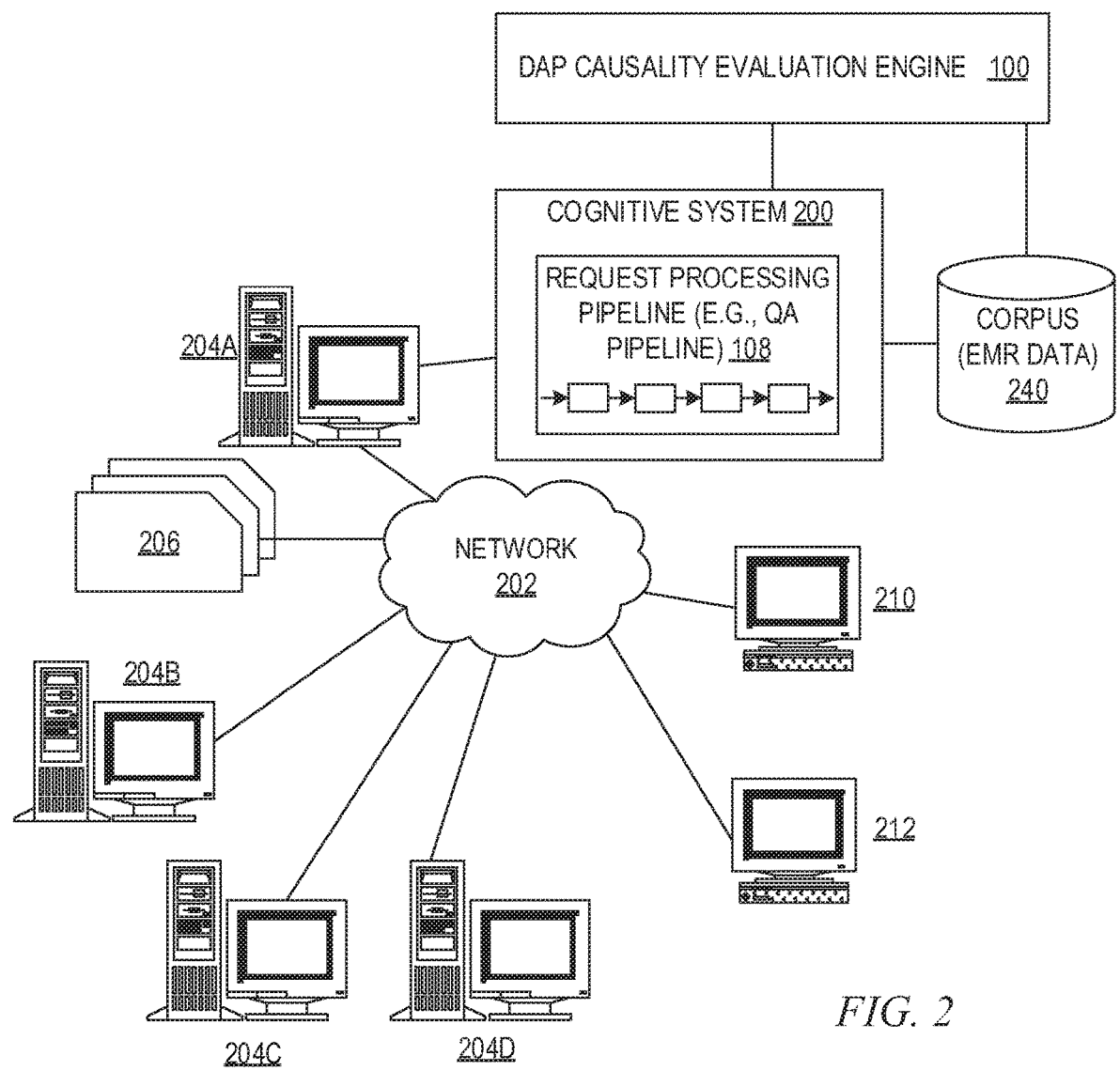
FIG. 2 depicts a schematic diagram of one illustrative embodiment of a cognitive healthcare system in a computer network.
Figure 3:
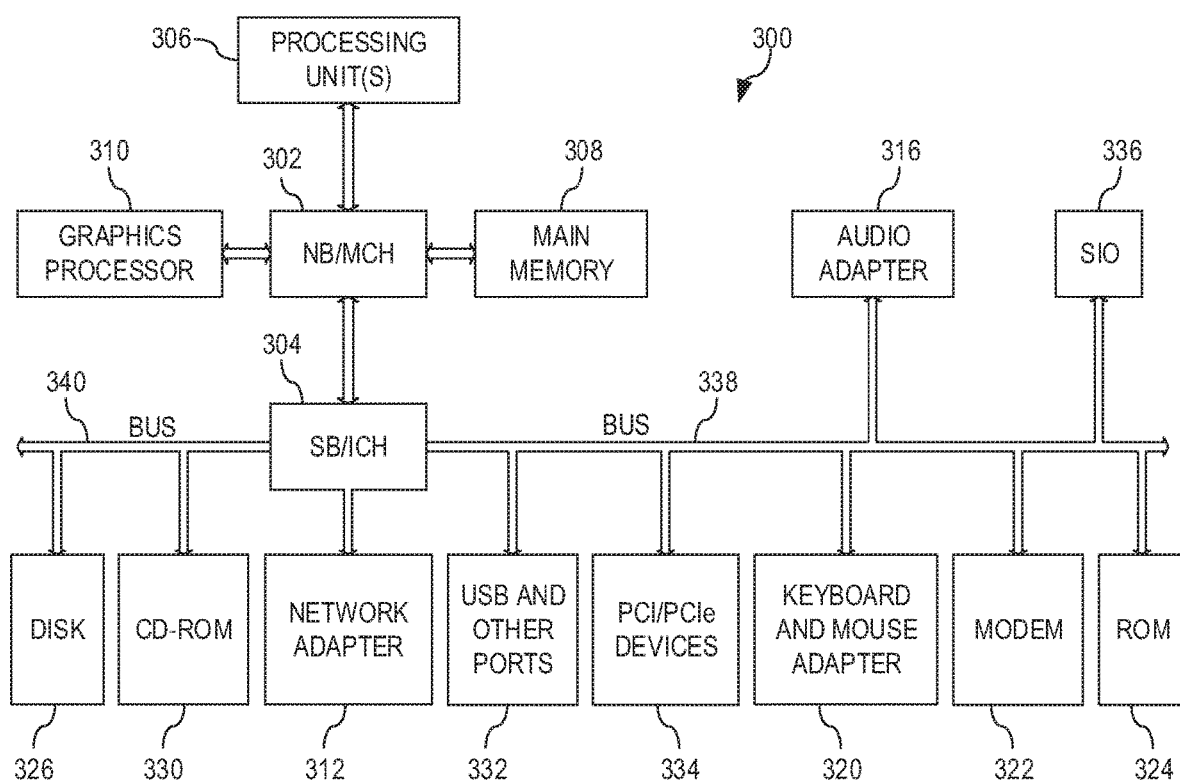
FIG. 3 is a block diagram of an example data processing system in which aspects of the illustrative embodiments are implemented.

It is clear from the above, that the illustrative embodiments may be utilized in many different types of data processing environments. In order to provide a context for the description of the specific elements and functionality of the illustrative embodiments, FIGS. 2-3 are provided hereafter as example environments in which aspects of the illustrative embodiments may be implemented. It should be appreciated that FIGS. 2-3 are only examples and are not intended to assert or imply any limitation with regard to the environments in which aspects or embodiments of the present invention may be implemented. Many modifications to the depicted environments may be made without departing from the spirit and scope of the present invention.

It should be noted that the mechanisms of the illustrative embodiments need not be utilized with a cognitive system. To the contrary, the illustrative embodiments may be implemented as a standalone DAP causality evaluation engine implemented on one or more computing devices or systems. The standalone DAP causality evaluation engine may generate an output notification that may be utilized by a user when evaluating a particular drug, adverse event, or the combination of drug and adverse event. Thus, in a standalone implementation, the DAP causality evaluation engine may be implemented using one or more computing devices or systems such as depicted in FIG. 3, as one example. However, to illustrate further functionality of illustrative embodiments of the present invention, FIGS. 2-3 are provided to illustrate the way in which the DAP causality evaluation engine may be utilized with a cognitive system to perform cognitive healthcare operations for diagnosing or treating a patient.

FIGS. 2-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for providing treatment recommendations for a patient at least partially based on the predictions of causality of drug-adverse event (or adverse drug reaction) pairs generated by the DAP causality evaluation engine of the illustrative embodiments.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

The request processing pipelines may utilize the predictions generated by the DAP causality evaluation engine of one or more of the illustrative embodiments, such as the DAP causality evaluation engine 100 in FIG. 1, as a factor considered by the request processing pipeline when performing cognitive evaluations of a patient to determine a diagnosis of the patient, determine a recommended treatment for the patient, and/or monitor the patient, with an aim at minimizing adverse drug reactions for drugs taken by the patient. Thus, for example, when evaluating various candidate treatments for the patient's medical condition, one factor that may be considered is the prediction of adverse drug reactions that may occur due to drugs that are part of the candidate treatments, as may be determined by the DAP causality evaluation engine. In cases where the cognitive healthcare system is using a pipeline to diagnose the patient, drugs being taken by the patient may be evaluated by the DAP causality evaluation engine to determine if there is a high enough probability that the drug may be the cause of a particular adverse event or adverse drug reaction associated with a medical condition of the patient, e.g., drug A causes a rash in patients that have a particular characteristic. Various other types of cognitive evaluations may also be implemented in which at least one of the factors considered may be the predictions generated by the DAP causality evaluation engine of the illustrative embodiments, without departing from the spirit and scope of the present invention.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments for generating predictions of drug-adverse event (or adverse drug reactions). It should be appreciated that while embodiments of the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?", the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As discussed herein, the illustrative embodiments may be integrated in, augment, and extend the functionality of these QA pipeline, or request processing pipeline, mechanisms of a healthcare cognitive system with regard to evaluating drug-adverse event pairings and generating predictions of whether or not a drug likely causes a particular adverse event. The predictions may then be utilized by the cognitive system as an additional factor for evaluating candidates answers or responses generated by the QA pipeline. For example, the predictions may be utilized when evaluating candidate diagnoses of the patient or evaluating candidate treatments for the patient.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 2-3 are only examples and are not intended to state or imply any limitation with regard to the type of cognitive system mechanisms with which the illustrative embodiments are implemented. Many modifications to the example cognitive system shown in FIGS. 2-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:
  Navigate the complexities of human language and understanding
  Ingest and process vast amounts of structured and unstructured data
  Generate and evaluate hypothesis
  Weigh and evaluate responses that are based only on relevant evidence
  Provide situation-specific advice, insights, and guidance
  Improve knowledge and learn with each iteration and interaction through machine learning processes
  Enable decision making at the point of impact (contextual guidance)
  Scale in proportion to the task
  Extend and magnify human expertise and cognition
  Identify resonating, human-like attributes and traits from natural language
  Deduce various language specific or agnostic attributes from natural language
  High degree of relevant recollection from data points (images, text, voice) (memorization and recall)
  Predict and sense with situational awareness that mimic human cognition based on experiences
  Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest-ranking score or confidence measure, or which is a best match to the input question, or a combination of ranked listing and final answer.

With regard to the DAP causality evaluation engine of the illustrative embodiments, the predictions generated by the DAP causality evaluation engine may be input to the QA pipeline for use as yet another portion of the corpus or corpora upon which the QA pipeline operates. For example, the predictions generated by the DAP causality evaluation engine may be included in inputs upon which the operations of the reasoning algorithms are applied, as part of the evaluation of evidence supporting various candidate answers or responses generated by the QA pipeline, or the like. Thus, the reasoning algorithms may include factors for evaluating the predictions of adverse drug reactions for drugs and adjusting scores for candidate diagnoses, treatments, or the like. For example, if a drug of a candidate treatment is likely to cause an adverse drug reaction, and the severity of that adverse drug reaction is sufficiently high according to the logic of the reasoning algorithm, then the score for the candidate treatment may be reduced such that it is ranked relatively lower than other candidate treatments for the patient.

FIG. 2 depicts a schematic diagram of one illustrative embodiment of a cognitive system 200 implementing a request processing pipeline 208, which in some embodiments may be a question answering (QA) pipeline, in a computer network 202. For purposes of the present description, it will be assumed that the request processing pipeline 208 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 200 is implemented on one or more computing devices 204A-D (comprising one or more processors and one or more memories, and potentially any other computing device elements generally known in the art including buses, storage devices, communication interfaces, and the like) connected to the computer network 202. For purposes of illustration only, FIG. 2 depicts the cognitive system 200 being implemented on computing device 204A only, but as noted above the cognitive system 200 may be distributed across multiple computing devices, such as a plurality of computing devices 204A-D. The network 202 includes multiple computing devices 204A-D, which may operate as server computing devices, and 210-212 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 200 and network 202 enables question processing and answer generation (QA) functionality for one or more cognitive system users via their respective computing devices 210-212. In other embodiments, the cognitive system 200 and network 202 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 200 may be used with components, systems, subsystems, and/or devices other than those that are depicted herein.

The cognitive system 200 is configured to implement a request processing pipeline 208 that receive inputs from various sources. The requests may be posed in the form of a natural language question, natural language request for information, natural language request for the performance of a cognitive operation, or the like. For example, the cognitive system 200 receives input from the network 202, a corpus or corpora of electronic documents 206, cognitive system users, and/or other data and other possible sources of input. In one embodiment, some or all of the inputs to the cognitive system 200 are routed through the network 202. The various computing devices 204A-D on the network 202 include access points for content creators and cognitive system users. Some of the computing devices 204A-D include devices for a database storing the corpus or corpora of data 206 (which is shown as a separate entity in FIG. 2 for illustrative purposes only). Portions of the corpus or corpora of data 206 may also be provided on one or more other network attached storage devices, in one or more databases, or other computing devices not explicitly shown in FIG. 2. The network 202 includes local network connections and remote connections in various embodiments, such that the cognitive system 200 may operate in environments of any size, including local and global, e.g., the Internet.

In one embodiment, the content creator creates content in a document of the corpus or corpora of data 206 for use as part of a corpus of data with the cognitive system 200. The document includes any file, text, article, or source of data for use in the cognitive system 200. Cognitive system users access the cognitive system 200 via a network connection or an Internet connection to the network 202, and input questions/requests to the cognitive system 200 that are answered/processed based on the content in the corpus or corpora of data 206. In one embodiment, the questions/requests are formed using natural language. The cognitive system 200 parses and interprets the question/request via a pipeline 208, and provides a response to the cognitive system user, e.g., cognitive system user 210, containing one or more answers to the question posed, response to the request, results of processing the request, or the like. In some embodiments, the cognitive system 200 provides a response to users in a ranked list of candidate answers/responses while in other illustrative embodiments, the cognitive system 200 provides a single final answer/response or a combination of a final answer/response and ranked listing of other candidate answers/responses.

The cognitive system 200 implements the pipeline 208 which comprises a plurality of stages for processing an input question/request based on information obtained from the corpus or corpora of data 206. The pipeline 208 generates answers/responses for the input question or request based on the processing of the input question/request and the corpus or corpora of data 206.

In some illustrative embodiments, the cognitive system 200 may be the IBM Watson™ cognitive system available from International Business Machines Corporation of Armonk, New York, which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 206. Based on the application of the queries to the corpus or corpora of data 206, a set of hypotheses, or candidate answers/responses to the input question/request, are generated by looking across the corpus or corpora of data 206 for portions of the corpus or corpora of data 206 (hereafter referred to simply as the corpus 206) that have some potential for containing a valuable response to the input question/response (hereafter assumed to be an input question). The pipeline 208 of the IBM Watson™ cognitive system then performs deep analysis on the language of the input question and the language used in each of the portions of the corpus 206 found during the application of the queries using a variety of reasoning algorithms.

The scores obtained from the various reasoning algorithms are then weighted against a statistical model that summarizes a level of confidence that the pipeline 208 of the IBM Watson™ cognitive system 200, in this example, has regarding the evidence that the potential candidate answer is inferred by the question. This process is repeated for each of the candidate answers to generate ranked listing of candidate answers which may then be presented to the user that submitted the input question, e.g., a user of client computing device 210, or from which a final answer is selected and presented to the user. More information about the pipeline 208 of the IBM Watson™ cognitive system 200 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 200 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result. In particular, the mechanisms of the healthcare based cognitive system may process predictions of drug-adverse event or adverse drug reaction pairings when performing the healthcare oriented cognitive system result, e.g., a diagnosis or treatment recommendation.

In the context of the present invention, cognitive system 200 may provide a cognitive functionality for assisting with healthcare based operations. For example, depending upon the particular implementation, the healthcare based operations may comprise patient diagnostics, medical treatment recommendation systems, personal patient care plan generation and monitoring, patient electronic medical record (EMR) evaluation for various purposes, such as for identifying patients that are suitable for a medical trial or a particular type of medical treatment, or the like. Thus, the cognitive system 200 may be a healthcare cognitive system 200 that operates in the medical or healthcare type domains and which may process requests for such healthcare operations via the request processing pipeline 208 input as either structured or unstructured requests, natural language input questions, or the like. In one illustrative embodiment, the cognitive system 200 is a medical treatment recommendation system that analyzes a patient's electronic medical records (EMRs) in relation to medical guidelines and other medical documentation in a corpus of information, and further the predictions of drug-adverse event (AE) or adverse drug reactions (ADRs) as generated by the DAP causality evaluation engine of the illustrative embodiments, to generate a recommendation as to how to treat a medical condition of the patient with minimal adverse events or adverse drug reactions.

As shown in FIG. 2, the cognitive system 200 is further augmented, in accordance with the mechanisms of the illustrative embodiments, to include logic implemented in specialized hardware, software executed on hardware, or any combination of specialized hardware and software executed on hardware, for implementing a DAP causality evaluation engine 100. As described previously, the DAP causality evaluation engine 100 evaluates drug-adverse event (or adverse drug reaction) pairings and generates predictions of whether a particular drug is a cause of a particular AE or ADR. The predictions may include an integrated causality score which may be included in the evaluation of evidence when generating candidate answers/ responses and/or evaluating evidential support for already identified candidate answers/responses. Thus, candidates identified by the cognitive system 200, whether those candidates are candidate diagnoses or candidate treatment recommendations, or the like, may have their ranking relative to other candidates affected by the identified predictions generated by the DAP causality evaluation engine 100.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 3 is provided as an example of one type of data processing system in which aspects of the present invention may be implemented. Many other types of data processing systems may be likewise configured to specifically implement the mechanisms of the illustrative embodiments.

FIG. 3 is a block diagram of an example data processing system in which aspects of the illustrative embodiments are implemented. Data processing system 300 is an example of a computer, such as server 204A or client 210 in FIG. 2, in which computer usable code or instructions implementing the processes for illustrative embodiments of the present invention are located. In one illustrative embodiment, FIG. 3 represents a server computing device, such as a server 204, which, which implements a cognitive system 200 and QA system pipeline 208 augmented to include the additional mechanisms of the illustrative embodiments described hereafter.

In the depicted example, data processing system 300 employs a hub architecture including North Bridge and Memory Controller Hub (NB/MCH) 302 and South Bridge and Input/Output (I/O) Controller Hub (SB/ICH) 304. Processing unit 306, main memory 308, and graphics processor 310 are connected to NB/MCH 302. Graphics processor 310 is connected to NB/MCH 302 through an accelerated graphics port (AGP).

In the depicted example, local area network (LAN) adapter 312 connects to SB/ICH 304. Audio adapter 316, keyboard and mouse adapter 320, modem 322, read only memory (ROM) 324, hard disk drive (HDD) 326, CD-ROM drive 330, universal serial bus (USB) ports and other communication ports 332, and PCI/PCIe devices 334 connect to SB/ICH 304 through bus 338 and bus 340. PCI/PCIe devices may include, for example, Ethernet adapters, add-in cards, and PC cards for notebook computers. PCI uses a card bus controller, while PCIe does not. ROM 324 may be, for example, a flash basic input/output system (BIOS).

HDD 326 and CD-ROM drive 330 connect to SB/ICH 304 through bus 340. HDD 326 and CD-ROM drive 330 may use, for example, an integrated drive electronics (IDE) or serial advanced technology attachment (SATA) interface. Super I/O (SIO) device 336 is connected to SB/ICH 304.

An operating system runs on processing unit 306. The operating system coordinates and provides control of various components within the data processing system 300 in FIG. 3. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 300.

As a server, data processing system 300 may be, for example, an IBM® eServer™ System p® computer system, running the Advanced Interactive Executive) (AIX®) operating system or the LINUX® operating system. Data processing system 300 may be a symmetric multiprocessor (SMP) system including a plurality of processors in processing unit 306. Alternatively, a single processor system may be employed.

Instructions for the operating system, the object-oriented programming system, and applications or programs are located on storage devices, such as HDD 326, and are loaded into main memory 308 for execution by processing unit 306. The processes for illustrative embodiments of the present invention are performed by processing unit 306 using computer usable program code, which is located in a memory such as, for example, main memory 308, ROM 324, or in one or more peripheral devices 326 and 330, for example.

A bus system, such as bus 338 or bus 340 as shown in FIG. 3, is comprised of one or more buses. Of course, the bus system may be implemented using any type of communication fabric or architecture that provides for a transfer of data between different components or devices attached to the fabric or architecture. A communication unit, such as modem 322 or network adapter 312 of FIG. 3, includes one or more devices used to transmit and receive data. A memory may be, for example, main memory 308, ROM 324, or a cache such as found in NB/MCH 302 in FIG. 3.

Those of ordinary skill in the art will appreciate that the hardware depicted in FIGS. 2 and 3 may vary depending on the implementation. Other internal hardware or peripheral devices, such as flash memory, equivalent non-volatile memory, or optical disk drives and the like, may be used in addition to or in place of the hardware depicted in FIGS. 2 and 3. Also, the processes of the illustrative embodiments may be applied to a multiprocessor data processing system, other than the SMP system mentioned previously, without departing from the spirit and scope of the present invention.

Moreover, the data processing system 300 may take the form of any of a number of different data processing systems including client computing devices, server computing devices, a tablet computer, laptop computer, telephone or other communication device, a personal digital assistant (PDA), or the like. In some illustrative examples, data processing system 300 may be a portable computing device that is configured with flash memory to provide non-volatile memory for storing operating system files and/or user-generated data, for example. Essentially, data processing system 300 may be any known or later developed data processing system without architectural limitation.

Figure 4:
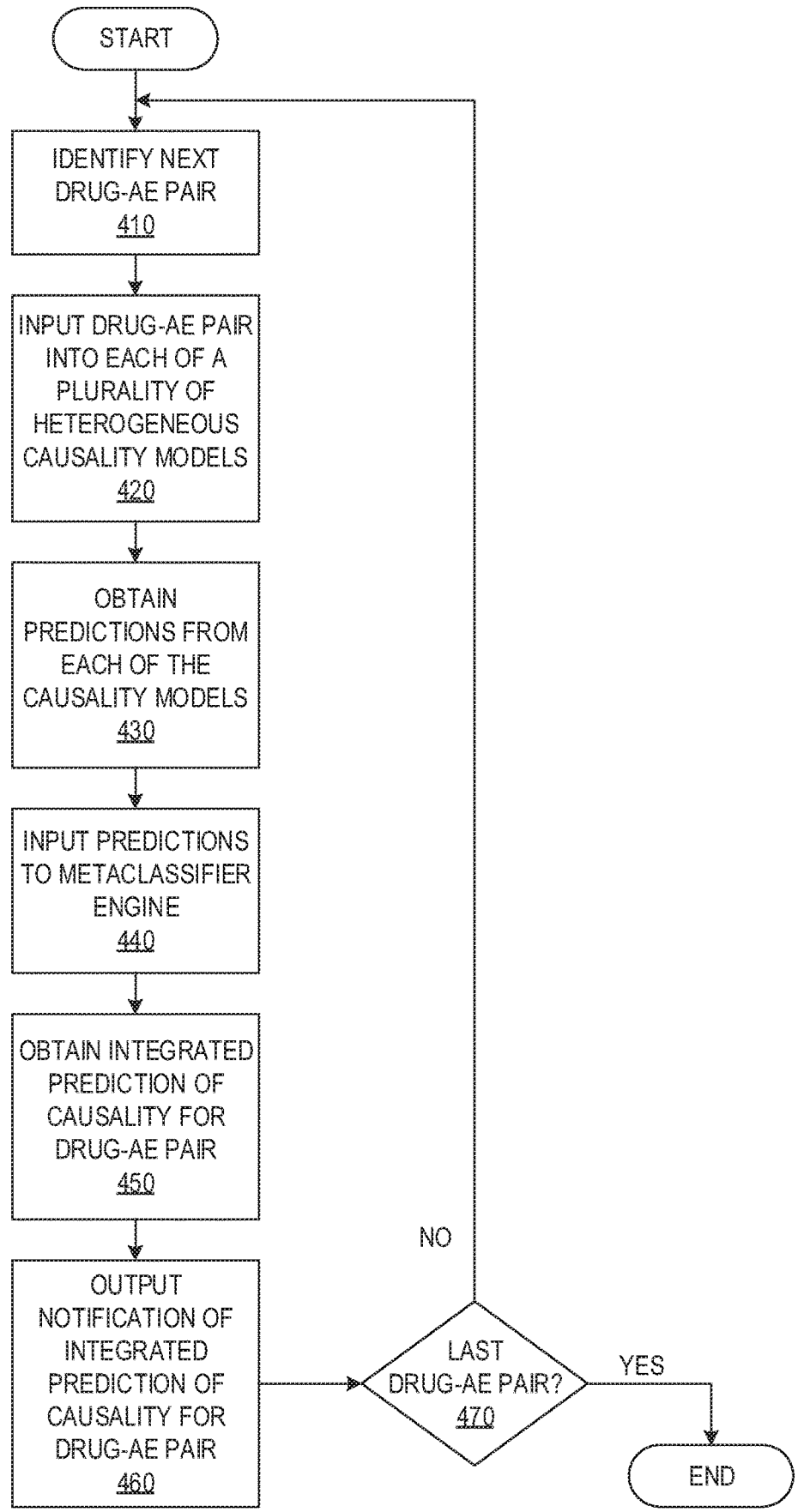
FIG. 4 is a flowchart outlining an example operation of a drug-AE pair causality evaluation engine in accordance with one illustrative embodiment.

FIG. 4 is a flowchart outlining an example operation of a drug-AE pair causality evaluation engine in accordance with one illustrative embodiment. As shown in FIG. 4, the operation starts by identifying a next drug-AE pair to evaluate (step 410). The identification of a next drug-AE pair to evaluate may be performed in various ways depending on the particular implementation. For example, if a listing of drugs is provided for evaluation, each of the drugs in the listing may be used to generate a drug-AE pairing based on known AEs that the system is configured to evaluate. In implementations where the AE is provided, the AE may be paired with each of a plurality of drugs for which the system is configured to evaluate to generate a plurality of drug-AE pairings. In still other implementations, a patient EMR may be analyzed to identify a listing of drugs, a listing of one or more adverse events, as well as characteristics of the patient, such that each combination of drug and adverse event from the listings may be evaluated along with characteristics of the patient to determine predictions with regard to the drug causing the adverse event.

The drug-AE is input to each of a plurality of heterogeneous causality models which evaluate corresponding causality factors of the drug and AE (step 420). Each causality model generates a prediction with a causality score and corresponding risk factor label, e.g., 0.8 (80%) and risk factor label of 1 or 0 as to whether the AE will or will not happen (step 430). The plurality of predictions generated by the causality models are input to a metaclassifier engine (step 440) that integrates the predictions to generate a single integrated causality prediction for the drug-AE pairing (step 450) which is then output (step 460). A determination is made as to whether this is the final drug-AE pairing to be evaluated (step 470). If not, the operation returns to step 410 with the next drug-AE pairing being identified. If this is the last drug-AE pairing to be evaluated, the operation terminates.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions that are executed by the at least one processor to cause the at least one processor to be configured to implement a plurality of heterogeneous computer executed causality models and a metaclassifier, the method comprising:

executing on each computer executed causality model in the plurality of heterogenous computer executed causality models, machine learning training operations, based on multi-dimensional drug profile training data comprising characteristic features of a plurality of drugs and adverse events (AEs), to train the computer executed causality model to generate risk predictions for drug and AE pairings at least by processing a corresponding set of causality factors, wherein each computer executed causality model is configured to evaluate a different corresponding set of causality factors than other computer executed causality models in the plurality of heterogenous computer executed causality models;

analyzing a patient electronic medical record (EMR) to identify at least one of a listing of drugs being taken by a patient or a listing of AEs associated with the patient, generating a drug and AE based on at least one of the listing of drugs being taken by the patient or the listing of AEs associated with the patient, wherein at least one of the drug in the drug and AE pair is a drug selected from the listing of drugs, or the AE in the drug and AE pair is one of the AEs in the listing of AEs;

processing, by each computer executed causality model in the plurality of heterogenous computer executed causality models, drug information for the drug to generate a plurality of risk predictions for the drug and AE pair, wherein each computer executed causality model generates a corresponding separate risk prediction, in the plurality of risk predictions, for the drug and AE pair, and wherein each of the risk predictions include at least one of a risk score or a risk label indicating a probability of the AE occurring with use of the drug;

providing, by the plurality of heterogenous computer executed causality models, the risk predictions to a metaclassifier, wherein the metaclassifier is a computer executed model that is trained, by machine learning based training operations, to aggregate risk predictions from the plurality of heterogenous computer executed causality models at least by executing a weighted aggregation by applying corresponding learned weight values to different risk predictions in the plurality of risk predictions and combining the resulting weighted risk predictions;

generating, by the metaclassifier, a single causality score value indicative of a probability of causality between the drug and the AE, of the drug and AE pair, based on the weighted aggregation of the risk predictions from the plurality of heterogenous causality models; and outputting, by the metaclassifier, the single causality score value in association with information identifying the drug and AE pair.

2. The method of claim 1, wherein outputting the single score comprises outputting detailed causal features via feature selection technology and statistics tests.

3. The method of claim 1, wherein generating the single causality score value comprises:

weighting, by the metaclassifier, each risk prediction of the plurality of risk predictions from the plurality of heterogenous causality models based on a corresponding learned weight value for a heterogenous computer executed causality model learned by the metaclassifier through a machine learning process, to thereby generate weighted risk predictions; and aggregating, by the metaclassifier, the weighted risk predictions to generate the single causality score value, wherein the metaclassifier applies different learned weight values to different risk predictions from different computer executed causality models in the plurality of heterogeneous computer executed causality models.

4. The method of claim 1, wherein the plurality of heterogeneous computer executed causality models comprise at least one of a chemical structure properties risk prediction computer executed model, a drug-drug interaction properties risk prediction computer executed model, a protein structure properties risk prediction computer executed model, a drug-food interaction risk prediction computer executed model, a drug-disease interaction risk prediction computer executed model, a temporal cues risk prediction computer executed model, or a dechallenge/rechallenge characteristics risk prediction computer executed model.

5. The method of claim 1, further comprising:

comparing, by the metaclassifier, the single causality score value to at least one threshold indicating a minimum causality score value required to identify a valid causality link between the drug and the adverse event; and outputting, by the metaclassifier, an output indicating whether or not there is a valid causality link between the drug and the adverse event based on results of the comparison.

6. The method of claim 1, wherein analyzing the patient EMR identifies a listing of drugs being taken by the patient, wherein the drug in the drug and AE pairing is a drug selected from the listing of drugs, and wherein the AE in the drug and AE pairing is one of a plurality of possible AEs for which the patient is being evaluated.

7. The method of claim 1, wherein analyzing the patient EMR identifies a listing of AEs associated with the patient, wherein the AE in the drug and AE pairing is an AE selected from the listing of AEs, and wherein the drug in the drug and AE pairing is one of a plurality of potential drugs that may cause the AE as identified from at least one drug data source.

8. The method of claim 1, wherein the method is performed for each of a plurality of drugs and for each of a plurality of AEs, and wherein each combination of a drug in the plurality of drugs with an AE in the plurality of AEs provides a pairing of the drug with the AE that is evaluated using the method.

9. The method of claim 1, wherein outputting, by the metaclassifier, the single causality score value comprises outputting the single causality score value to a cognitive system to perform a cognitive operation based on the single causality score, and wherein the cognitive operation comprises at least one of providing decision support for diagnosing a medical condition of a patient, wherein the medical condition is associated with the AE in the drug and AE pair, or providing decision support for providing a treatment recommendation that comprises the drug in the drug and AE pair.

10. The method of claim 1, wherein outputting, by the metaclassifier, the single causality score value comprises transmitting a notification message to a computing system associated with a provider of the drug in the drug and AE pair, indicating a probability that the drug causes the AE, in response to the single causality score value meeting or exceeding a predetermined threshold value.

11. A computer program product comprising a computer readable storage medium having a computer readable program stored therein, wherein the computer readable program when executed on a data processing system, causes the data processing system to implement a plurality of heterogeneous computer executed causality models and a metaclassifier, and further causes the data processing system to:
execute, on each computer executed causality model in the plurality of heterogenous computer executed causality models, machine learning training operations, based on multi-dimensional drug profile training data comprising characteristic features of a plurality of drugs and adverse events (AEs), to train the computer executed causality model to generate risk predictions for drug and AE pairings at least by processing a corresponding set of causality factors, wherein each computer executed causality model is configured to evaluate a different corresponding set of causality factors than other computer executed causality models in the plurality of heterogenous computer executed causality models;
analyze a patient electronic medical record(EMR) to identify at least one of a listing of drugs being taken by a patient or a listing of AEs associated with the patient, generating a drug and AE pair based on at least one of the listing of drugs being taken by the patient or the listing of AEs associated with the patient, wherein at least one of the drug in the drug and AE pair is a drug selected from the listing of drugs, or the AE in the drug and AE pair is one of the AEs in the listing of AEs;
process, by each computer executed causality model in the plurality of heterogenous computer executed causality models, drug information for the drug to generate a plurality of risk predictions for the drug and AE pair, wherein each computer executed causality model generates a corresponding separate risk prediction, in the plurality of risk predictions, for the drug and AE pair, and wherein each of the risk predictions include at least one of a risk score or a risk label indicating a probability of the AE occurring with use of the drug;
provide, by the plurality of heterogenous computer executed causality models, the risk predictions to a metaclassifier, wherein the metaclassifier is a computer executed model that is trained, by machine learning based training operations, to aggregate risk predictions from the plurality of heterogenous computer executed causality models at least by executing a weighted aggregation by applying corresponding learned weight values to different risk predictions in the plurality of risk predictions and combining the resulting weighted risk predictions;
generate, by the metaclassifier, a single causality score value indicative of a probability of causality between the drug and the AE, of the drug and AE pair, based on the weighted aggregation of the risk predictions from the plurality of heterogenous causality models; and
output, by the metaclassifier, the single causality score value in association with information identifying the drug and AE pair.

12. The computer program product of claim 11, wherein the computer readable program further causes the data processing system to output the single score at least by outputting detailed causal features via feature selection technology and statistics tests.

13. The computer program product of claim 11, wherein the computer readable program further causes the data processing system to generate the single causality score value at least by:
weighting, by the metaclassifier, each risk prediction of the plurality of risk predictions from the plurality of heterogenous causality models based on a corresponding learned weight value for a heterogenous computer executed causality model learned by the metaclassifier through a machine learning process, to thereby generate weighted risk predictions; and
aggregating, by the metaclassifier, the weighted risk predictions to generate the single causality score value, wherein the metaclassifier applies different learned weight values to different risk predictions from different computer executed causality models in the plurality of heterogeneous computer executed causality models.

14. The computer program product of claim 11, wherein the plurality of heterogeneous computer executed causality models comprise at least one of a chemical structure properties risk prediction computer executed model, a drug-drug interaction properties risk prediction computer executed model, a protein structure properties risk prediction computer executed model, a drug-food interaction risk prediction computer executed model, a drug-disease interaction risk prediction computer executed model, a temporal cues risk prediction computer executed model, or a dechallenge/rechallenge characteristics risk prediction computer executed model.

15. The computer program product of claim 11, wherein the computer readable program further causes the data processing system to:
compare, by the metaclassifier, the single causality score value to at least one threshold indicating a minimum causality score value required to identify a valid causality link between the drug and the adverse event; and
output, by the metaclassifier, an output indicating whether or not there is a valid causality link between the drug and the adverse event based on results of the comparison.

16. The computer program product of claim 11, wherein the computer readable program further causes the data processing system to analyze the patient EMR to identify a listing of drugs being taken by the patient, wherein the drug in the drug and AE pairing is a drug selected from the listing of drugs, and wherein the AE in the drug and AE pairing is one of a plurality of possible AEs for which the patient is being evaluated.

17. The computer program product of claim 11, wherein the computer readable program further causes the data processing system to analyze the patient EMR to identify a listing of AEs associated with the patient, wherein the AE in the drug and AE pairing is an AE selected from the listing of AEs, and wherein the drug in the drug and AE pairing is one of a plurality of potential drugs that may cause the AE as identified from at least one drug data source.

18. The computer program product of claim 11, wherein the operation of the data processing system is performed for each of a plurality of drugs and for each of a plurality of AEs and wherein each combination of a drug in the plurality of drugs with an AE in the plurality of AEs provides a pairing of the drug with the AE that is evaluated by the operation of the data processing system.

19. The computer program product of claim 11, wherein the computer readable program further causes the data processing system to output, by the metaclassifier, the single causality score value at least by outputting the single causality score value to a cognitive system to perform a cognitive operation based on the single causality score, and wherein the cognitive operation comprises at least one of providing decision support for diagnosing a medical condition of a patient, wherein the medical condition is associated with the AE in the drug and AE pair, or providing decision support for providing a treatment recommendation that comprises the drug in the drug and AE pair.

20. A data processing system comprising:
 at least one processor; and
 at least one memory coupled to the at least one processor, wherein the at least one memory comprises instructions which, when executed by the at least one processor, cause the at least one processor to implement a plurality of heterogeneous computer executed causality models and a metaclassifier and further cause the at least one processor to:
execute, on each computer executed causality model in the plurality of heterogenous computer executed causality models, machine learning training operations, based on multi-dimensional drug profile training data comprising characteristic features of a plurality of drugs and adverse events (AEs), to train the computer executed causality model to generate risk predictions for drug and AE pairings at least by processing a corresponding set of causality factors, wherein each computer executed causality model is configured to evaluate a different corresponding set of causality factors than other computer executed causality models in the plurality of heterogenous computer executed causality models;

analyze, a patient electronic medical record (EMR) to identify at least one of a listing of drugs being taken by a patient or a listing of AEs associated with the patient, generating a drug and AE pair based on at least one of the listing of drugs being taken by the patient or the listing of AEs associated with the patient, wherein at least one of the drug in the drug and AE pair is a drug selected from the listing of drugs or the AE in the drug and AE pair is one of the AEs in the listing of AEs;

process, by each computer executed causality model in the plurality of heterogenous computer executed causality models, drug information for the drug to generate a plurality of risk predictions for the drug and AE pair, wherein each computer executed causality model generates a corresponding separate risk prediction, in the plurality of risk predictions, for the drug and AE pair and wherein each of the risk predictions include at least one of a risk score or a risk label indicating a probability of the AE occurring with use of the drug;

provide, by the plurality of heterogenous computer executed causality models, the risk predictions to a metaclassifier, wherein the metaclassifier is a computer executed model that is trained, by machine learning based training operations, to aggregate risk predictions from the plurality of heterogenous computer executed causality models at least by executing a weighted aggregation by applying corresponding learned weight values to different risk predictions in the plurality of risk predictions and combining the resulting weighted risk predictions;

generate, by the metaclassifier, a single causality score value indicative of a probability of causality between the drug and the AE, of the drug and AE pair, based on the weighted aggregation of the risk predictions from the plurality of heterogenous causality models; and output, by the metaclassifier, the single causality score value in association with information identifying the drug and AE pair.

\* \* \* \* \*